United States Patent
Chiu et al.

(10) Patent No.: US 8,062,903 B2
(45) Date of Patent: Nov. 22, 2011

(54) DROPLET COMPARTMENTALIZATION FOR CHEMICAL SEPARATION AND ON-LINE SAMPLING

(75) Inventors: Daniel T. Chiu, Seattle, WA (US); John Scott Edgar, Kirkland, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 12/397,209

(22) Filed: Mar. 3, 2009

(65) Prior Publication Data

US 2009/0217742 A1    Sep. 3, 2009

Related U.S. Application Data

(60) Provisional application No. 61/033,281, filed on Mar. 3, 2008.

(51) Int. Cl.
*G01N 1/18* (2006.01)
(52) U.S. Cl. ........... 436/174; 436/53; 422/82; 73/64.56; 73/61.55; 73/61.44; 250/288; 204/450
(58) Field of Classification Search .............. None
See application file for complete search history.

(56) References Cited

U.S. PATENT DOCUMENTS

| | | | |
|---|---|---|---|
| 2003/0201022 A1* | 10/2003 | Kawai et al. ............ | 137/828 |
| 2005/0087122 A1* | 4/2005 | Ismagliov et al. ........ | 117/2 |
| 2006/0096923 A1* | 5/2006 | Wagler et al. ............ | 210/656 |
| 2008/0014589 A1 | 1/2008 | Link | |

OTHER PUBLICATIONS

Edgar et al. "Compartmentalization of Chemically Separated Components into Droplets," Angew. Chem. Int. Ed. 2009, 48, 2719-2722, available online Jan. 13, 2009.*
He et al. "Selective Encapsulation of Single Cells and Subsellular Organelles into Picoliter- and Femtoliter-Volume Droplets," Anal. Chem. 2005, 77, 1539-1544.*
Tan et al. "A trap-and-release integrated microfluidic system for dynamic microarray applications," PNAS, 2007, 104, 1146-1151.*
Chasteen, T. G. "Capillary Electrophoresis," 2005, URL <http://www.shsu.edu/~chm_tgc/primers/pdf/CE.pdf>, downloaded from the internet on Oct. 23, 2003.*
Liau, A. et al. "Mixing Crowded Biological Solutions in Milliseconds," Anal. Chem. 2005, 77, 7618-7625.*
Smith, R. D. et al. "Capillary Zone Electrophoresis-Mass Spectrometry Using an Electrospray Ionization Interface," Anal. Chem. 1988, 60, 436-441.*
Johnson, T. et al. "A CE-MALDI Interface Based on the Use of Prestructured Sample Supports," Anal. Chem. 2001, 73, 1670-1675.*
Shi, W., et al., "Droplet-Based Microfluidic System for Individual *Caenorhabditis elegans* Assay," Lab Chip 8(9):1432-1435, Sep. 2008.

* cited by examiner

*Primary Examiner* — Yelena G Gakh
*Assistant Examiner* — Michelle Adams
(74) *Attorney, Agent, or Firm* — Christensen O'Connor Johnson Kindness PLLC

(57) ABSTRACT

Methods and devices are provided for overcoming detrimental diffusive effects in a sample liquid stream by forming segmented liquid bodies (e.g., droplets) from a sample liquid stream in an immiscible liquid stream. The liquid bodies are formed at the intersection of a channel providing the sample liquid stream and a channel providing the immiscible liquid stream. The formed liquid bodies compartmentalize the portion of the sample liquid stream from which the liquid bodies are formed, thus minimizing the detrimental effects of diffusion that occur in a continuous liquid stream.

14 Claims, 11 Drawing Sheets

DROPLET COMPARTMENTALIZATION FOR CHEMICAL SEPARATION AND ON-LINE SAMPLING

CROSS-REFERENCE TO RELATED APPLICATION

This application claims the benefit of U.S. Provisional Application No. 61/033,281, filed Mar. 3, 2008, expressly incorporated herein by reference in its entirety.

STATEMENT OF GOVERNMENT LICENSE RIGHTS

This invention was made with Government support under Grant No. EB005197 awarded by the National Institutes of Health. The Government has certain rights in the invention.

BACKGROUND OF THE INVENTION

The basic unit of a biological system is a single cell, and malfunctions at the single-cell level can result in devastating diseases, such as in cancer metastasis, where a single cell seeds the formation of a distant tumor. Given that a single cell contains a diverse set of molecules at low copy numbers, high-resolution and high-sensitivity techniques in microscale chemical separation play an important role in single-cell analysis. For many single-cell studies, it is insufficient simply to detect a series of separated peaks using fluorescence. Because of the complexity of the cellular contents, the detected peaks likely need to be further separated (e.g., a second-dimensional analysis) or analyzed with complementary high-sensitivity techniques.

In microscale separation, the goal is to separate individual analyte species of a complex mixture into distinct bands. After the detection of each band, however, the integrity of the separated components cannot be easily preserved for additional analysis or manipulation, owing to molecular diffusion. This challenge is especially acute in high-resolution liquid separation techniques, such as in capillary electrophoresis (CE) and microscale high-performance liquid chromatography (HPLC), because of the extremely small volumes and narrow bands involved and because molecular diffusion scales quadratically with the inverse of distance.

In CE, for example, sample volumes are often in the nanoliter range or smaller, and where the number of theoretical plates often range up to the millions. In some chip-based systems, or when very small-bore capillaries are used, sample volumes can range down to the femtoliter regime. In such systems, it is extremely difficult to maintain the contents of the separated peaks after their detection.

Attempts have been made to address the issue of material compartmentalization after separation. For example, elastomeric valves and sub-nanoliter chambers have been used to capture separated CE bands for single-molecule studies. In the context of two-dimensional (2D) CE separation, methods have been developed for interfacing two fused-silica CE capillaries such that the separated CE bands can be transferred from one capillary onto another for 2D separation and analysis.

Despite recent advances, a technique that allows for the preservation of chromatographically-separated liquid materials, such that further analysis of the materials can be performed while maintaining the integrity of the original separation, would allow for further improvements in liquid chromatography and related analytical techniques.

Relatedly, on-line sampling is required to monitor the progress of many chemical and biological processes, such as in chemical synthesis and bioreactors. In real-time sampling, however, the withdrawn samples are dispersed throughout the sampling tubing as a result of axial dispersion generated by the parabolic profile of the pressure-driven flow and because of the effects of diffusion. The methods currently employed to test such real-time reaction profiles have not provided a sufficient solution to the issues of dispersion and the inaccuracies in the resulting analyses that result from such dispersion.

In addition to sample dilution due to dispersion and diffusion effects, sample integrity in on-line sampling can be further compromised by contaminates deposited on the channel wall of the device during prior sample testing.

SUMMARY OF THE INVENTION

In one aspect, a method is provided for preserving the separation integrity of a chemically-separated liquid stream. In one embodiment, the method includes flowing a carrier liquid through a carrier channel to provide a carrier liquid stream and introducing a sample liquid, immiscible with the carrier liquid, through a sample channel into the carrier liquid stream at a rate sufficient to provide segmented liquid bodies of the sample liquid in the carrier liquid stream, the sample liquid including the effluent of a separatory device, the effluent including an analyte.

In another aspect, a device is provided for preserving the separation integrity of a chemically-separated liquid stream. In one embodiment, the device includes a carrier channel having an inlet and an outlet; a carrier liquid reservoir in liquid communication with the carrier channel inlet; a carrier liquid delivery means for delivering a carrier liquid from the carrier liquid reservoir to the carrier channel inlet at a first flow rate; a sample channel having an inlet and an outlet, where the sample channel outlet intersects the carrier channel intermediate the carrier channel inlet and carrier channel outlet; a liquid effluent outlet of a separatory device in liquid communication with the sample channel inlet; and a sample liquid delivery means for delivering a sample liquid from the liquid effluent outlet of the separatory device to the sample channel outlet at a second flow rate; where the first flow rate and the second flow rate are sufficient to form a liquid body of the sample liquid at the outlet of the sample channel.

In another aspect, a method is provided for preserving a liquid stream of an on-line sample of a reaction in a reaction vessel. In one embodiment, the method includes flowing a carrier liquid through a carrier channel to provide a carrier liquid stream and introducing a sample liquid, immiscible with the carrier liquid, through a sample channel into the carrier liquid stream at a rate sufficient to provide segmented liquid bodies of the sample liquid in the carrier liquid stream, the sample liquid including a stream of liquid extracted from a reaction vessel, the sample stream further including an analyte.

In another aspect, a device is provided for preserving a liquid stream of an on-line sample of a reaction in a reaction vessel. In one embodiment, the device includes a carrier channel having an inlet and an outlet; a carrier liquid reservoir in liquid communication with the carrier channel inlet; a carrier liquid delivery means for delivering a carrier liquid from the carrier liquid reservoir to the carrier channel inlet at a first flow rate; a sample channel having an inlet and an outlet, wherein the sample channel outlet intersects the carrier channel intermediate the carrier channel inlet and carrier channel outlet; a reaction vessel in liquid communication with the sample channel inlet; and a sample liquid delivery means for delivering a sample liquid from the reaction vessel to the sample channel outlet at a second flow rate; where the first flow rate and the second flow rate are sufficient to form a liquid body of the sample liquid at the outlet of the sample channel.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE INVENTION

Figure 1:
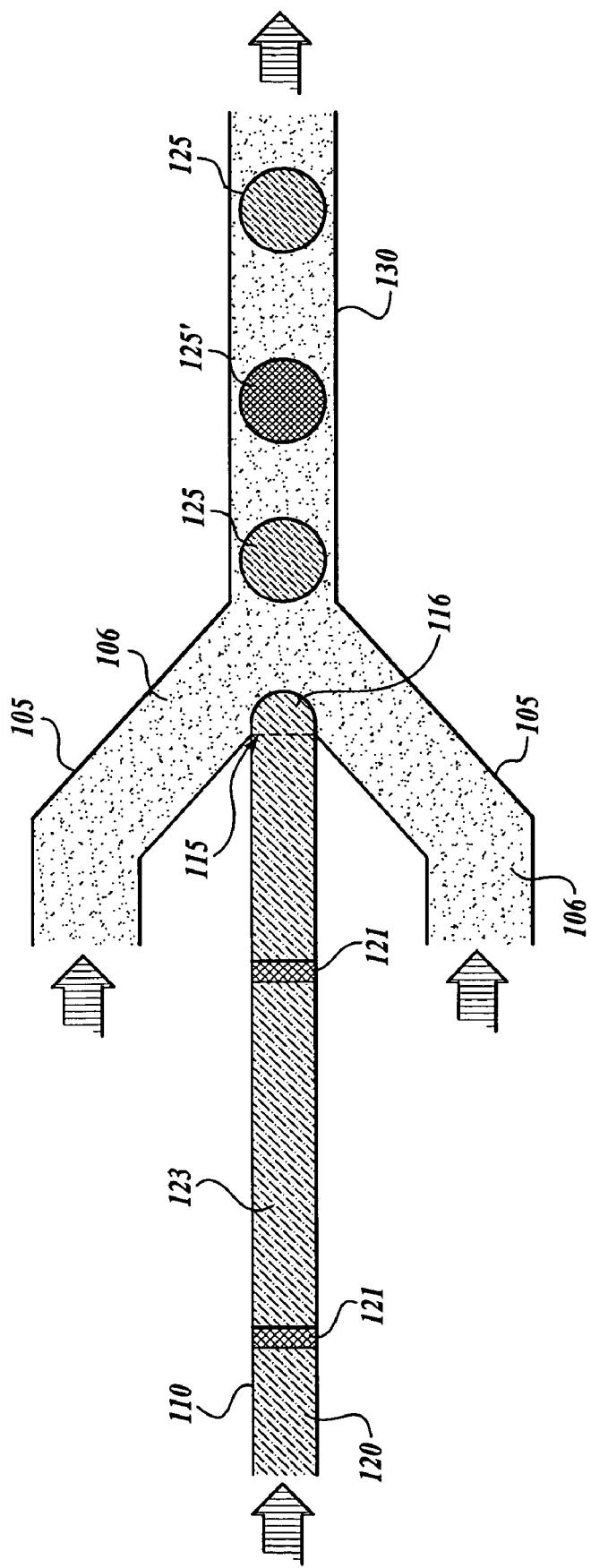
FIG. 1 is a diagrammatic illustration of a representative device useful for forming liquid bodies compartmentalizing an analyte in accordance with the invention.

Methods and devices are provided for generating liquid bodies (e.g., droplets) of a liquid following chemical separation or for on-line sampling. In a representative embodiment, the droplets comprise a liquid that is the effluent of a chromatographic separation (e.g., HPLC or CE). A carrier liquid ("carrier"), immiscible with the effluent liquid, surrounds the droplets and assists in their formation and transport. By compartmentalizing the separated effluent into a series of droplets, the separation effected by the chromatographic process is preserved and detrimental events, such as diffusion, are minimized. The droplets further enhance analysis of the effluent by providing the opportunity to continue analysis of the effluent past the primary detector (e.g., HPLC detector), and secondary (or further) analyses can be performed on the effluent without compromising the integrity of the chromatographic separation resulting from diffusion within the effluent volume.

In one aspect, a method is provided for preserving the separation integrity of a chemically-separated liquid stream. In one embodiment, the method includes flowing a carrier liquid through a carrier channel to provide a carrier liquid stream and introducing a sample liquid, immiscible with the carrier liquid, through a sample channel into the carrier liquid stream at a rate sufficient to provide segmented liquid bodies of the sample liquid in the carrier liquid stream, the sample liquid including the effluent of a separatory device, the effluent including an analyte.

In another aspect, a device is provided for preserving the separation integrity of a chemically-separated liquid stream. In one embodiment, the device includes a carrier channel having an inlet and an outlet; a carrier liquid reservoir in liquid communication with the carrier channel inlet; a carrier liquid delivery means for delivering a carrier liquid from the carrier liquid reservoir to the carrier channel inlet at a first flow rate; a sample channel having an inlet and an outlet, where the sample channel outlet intersects the carrier channel intermediate the carrier channel inlet and carrier channel outlet; a liquid effluent outlet of a separatory device in liquid communication with the sample channel inlet; and a sample liquid delivery means for delivering a sample liquid from the liquid effluent outlet of the separatory device to the sample channel outlet at a second flow rate; where the first flow rate and the second flow rate are sufficient to form a liquid body of the sample liquid at the outlet of the sample channel.

Methods and devices are provided for forming liquid bodies. As used herein, liquid bodies include droplets, which are spherical in shape, as well as non-spherical liquid bodies, such as plugs, which are liquid bodies within a channel that fill the cross-sectional area of the channel with liquid and extend longitudinally in the channel. Due to fluidic effects, even droplets and plugs that have dimensions that near the cross-sectional area of the channel in which they are disposed in may still be separated from contacting the channel walls by a thin layer of the carrier liquid.

The term "droplet," as used herein, is used to describe all liquid bodies, including liquid plugs. The liquid bodies are typically found in series, given the sequential temporal nature of embodiments of the invention. Thus, the liquid bodies typically appear segmented, such as is the case with a series of liquid plugs in a channel segmented by carrier liquid. In one embodiment the droplets are 100 microliters or less in volume. In a preferred embodiment, the droplets are 10 microliters or less in volume. In a further preferred embodiment, the droplets are 1 microliter or less in volume. In yet a further preferred embodiment, the droplets are 100 nanoliters or less in volume.

Representative devices of the invention operate under laminar flow conditions. While laminar flow is not required for the devices to operate, such flow conditions typically arise for the sub-milliliter-sized droplet volumes formed by preferred embodiments of the invention.

As used herein, the term "chemically separated" refers to any separation process by which at least two chemical species, introduced as a mixture, are separated. In a preferred embodiment, the sample liquid is the effluent of a chromatographic separation, such as capillary electrophoresis (CE), fused silica capillaries, size-exclusion columns, or high performance liquid chromatography (HPLC). Separation techniques compatible with the device include those techniques known to those of skill in the art. In one embodiment, separation is performed on a chromatographic or electrokinetic device. In a preferred embodiment, separation is performed using high-performance liquid chromatography or capillary electrophoresis. Representative separation techniques include high-performance liquid chromatography, ion exchange chromatography, size exclusion chromatography, ion exchange chromatography, bioaffinity chromatography, reverse phase chromatography, liquid chromatography, low-pressure liquid chromatography, open tubular liquid chromatography, magnetic chromatography, capillary electrophoresis, capillary zone electrophoresis (CZE), isotachophoresis (ITP), capillary isoelectric focusing (CIEF), capillary gel electrophoresis (CGE), micellar electrokinetic chromatography (MEKC), electrokinetic chromatography (EKC), micro emulsion electrokinetic chromatography (MEEKC), non aqueous capillary electrophoresis (NACE), and capillary electrochromatography. Representative separatory column materials useful in, for example, HPLC, include any separatory material capable of separating a chemical mixture, including stationary phases modified with C18, C8, phenyl, silica, pentafluorophenyl, cyano, and amino groups. HPLC columns may also include embedded polar groups, ion-exchange phases, and reverse-phase amides.

The effluent of the separation includes the sample liquid, which is directed towards the carrier liquid through a sample channel, adapted to communicate the sample liquid from the separatory device to the carrier liquid. The channel containing the sample liquid intersects a carrier channel at a junction. The carrier channel is adapted to provide and transport the carrier liquid, and droplets are formed when the sample liquid is forced into the carrier liquid at the junction. The droplets form in the carrier channel at the outlet of the sample channel.

The size of the droplets are defined by several factors, including the characteristics of the carrier liquid and the sample liquid, as well as the flow rates and pressures of the carrier liquid and the sample liquid. The dimensions of the carrier channel and sample channel also contribute to the size of the generated droplets. In one embodiment, the sample channel has a smaller lateral cross-sectional area than the lateral cross-sectional area of the carrier channel.

The frequency at which the droplets are generated, and the spacing between the droplets, are defined at least in part by the relative flow velocities of the carrier and sample liquids and the dimensions of the first and sample channels.

The carrier and sample liquids can be any liquid known to those of skill in the art, as long as the two liquids are immiscible to a substantial extent, such that droplets of the sample liquid can exist within the carrier liquid. In one embodiment, the sample liquid is a polar liquid and the carrier liquid is a non-polar liquid. In a representative embodiment, the sample liquid is an aqueous liquid containing analytes separated by a chromatographic process and the carrier liquid is an oil, thus creating an aqueous/oil interface and aqueous droplets generated in the oil. Representative oils useful as a carrier liquid include carbon-based oils, silicone-based oils, and fluorinated oils. Representative examples of oils useful in the invention include embryo-tested mineral oil, light mineral oil, heavy mineral oil, PCR mineral oil, AS4 silicone oil, AS 100 silicone oil, AR20 silicone oil, AR 200 silicone oil, AR 1000 silicone oil, AP 100 silicone oil, AP 1000 silicone oil, AP 150 silicone oil, AP 200 silicone oil, CR 200 Silicone oil, DC 200 silicone oil, DC702 silicone oil, DC 710 silicone oil, octanol, decanol, acetophenone, perfluoro-oils perfluorononane, perfluorodecane, perfluorodimethylcylcohexane, perfluoro-1-butanesulfonyl fluoride, perfluoro-1-octanesulfonyl fluoride, perfluoro-1-octanesulfonyl fluoride, nonafluoro-1-butanesulfonyl chloride, nonafluoro-tert-butyl alcohol, perfluorodecanol, perfluorohexane, perfluorooctanol, perfluorodecene, perfluorohexene, perfluorooctene, fuel oil, halocarbon oil 28, halocarbon oil 700, hydrocarbon oil, glycerol, 3M Fluoriner™ fluids (FC-40, FC-43, FC-70, FC-72, FC-77, FC-84, FC-87, FC-3283), soybean oil, castor oil, coconut oil, cedar oil, clove bud oil, fir oil, linseed oil, safflower oil, sunflower oil, almond seed oil, anise oil, clove oil, cottonseed oil, corn oil, croton oil, olive oil, palm oil, peanut oil, bay oil, borage oil, bergamot oil, cod liver oil, macadamia nut oil, camada oil, chamomile oil, citronella oil, eucalyptus oil, fennel oil, lavender oil, lemon oil, nutmeg oil orange oil, petitgrain oil, rose oil, tarragon oil, tung oil, basil oil, birch oil, black pepper oil, birch tar oil, carrot seed oil, cardamom oil, cassia oil, sage oil, cognac oil, copaiba balsam oil, cypress oil, eucalyptus oil, dillweed oil, grape fruit oil, ginger oil, juniper oil, lavender oil, lovage oil, majoram oil, mandarin oil, myrrh oil, neroli oil, olibanum oil, onion oil, paraffin oil, origanum oil, parsley oil, peppermint oil, pimenta leaf oil, sage oil, rosemary oil, rose oil, sandalwood oil, sassafras oil, spearmint oil, thyme oil, transformer oil, verbena oil, and rapeseed oil.

Upon formation of droplets, the droplets may be further manipulated using fluidic techniques known to those of skill in the art. In one embodiment, the droplets are analyzed to detect an analyte. In an exemplary embodiment, the droplets are directed in a fluidic channel towards an analytical element, such as a fluorescence detection device, for analysis. The droplets generated by the device have the benefit of maintaining the integrity of the separation of the chromatographic technique while allowing the liquid to be further manipulated and analyzed. In known techniques, a continuous stream of separated effluent is directed to secondary analytical stations, yet the continuous nature of the effluent stream results in mixing and diffusion of the analytes within the stream. The longer time and distance between separation and analysis leads to more diffusion and, thus, less accurate results. The droplets formed by the invention maintain the separation integrity and allow for secondary, tertiary, and further analyses of a separated liquid while maintaining separation integrity and the accuracy of the analyses.

In one embodiment, the device is formed from discrete components, such as channels connected together by junctions. Representative channel materials polymeric tubing, glass tubing, fused silica capillaries, Teflon®tubing, polyethylene tubing, and other materials known to those of skill in the art.

While microfluidic chip-based devices are a preferred embodiment of the invention, devices not based on chip architectures are also useful, for example the use of a zero-dead-volume T-interconnect (also referred to as a T-junction; illustrated in FIG. 5) that links the end of a separation capillary orthogonally to a second capillary where carrier liquid exits. A representative T-interconnect can be fabricated out of glass, metal, or polymeric substance. Additionally, interconnects can be fabricated from curable resins that mold specifically to any combination of separation channels and exit channels.

In one embodiment, the device is formed as a component of a microfluidic chip ("chip"). The term "on-chip" refers to processes occurring on a microfluidic chip and "off-chip" refers to processes occurring off the microfluidic chip. Droplets formed using microfluidics is particularly versatile because the frequency of droplet formation can be tuned from sub-Hz to thousands of Hz and the size of droplets can be adjusted from femtoliters to nanoliters. Additionally, the temperature of a continuous stream of flowing droplets can be altered over a very wide range without significantly affecting the physical properties of the immiscible carrier phase. The concentration of droplet-contained molecules also can be dynamically altered over several orders of magnitude without noticeable changes in droplet temperature, an attribute that is unique to such small-scale reaction vessels and which is difficult to attain with a macroscopic container.

Microfluidic chip devices can be fabricated with several different components on a single chip, and thus the devices of the invention are useful as one component among several on a chip. For example, a separatory device (e.g., a capillary electrophoresis device), a droplet-forming device of the invention, and an analytical technique (e.g., fluorescence spectroscopy) can all be integrated onto a chip together to provide a chip for separating, compartmentalizing, and analyzing a sample stream.

Device chips can be fabricated using techniques known to those of skill in the art, including traditional semiconductor processing techniques and soft lithographic techniques, such as molding and imprinting. In an exemplary embodiment, a device is fabricated on a silicon substrate with channels formed in a polymer (e.g., polydimethylsiloxane (PDMS)). The device can be formed from a single material (e.g., a polymer) or a combination of materials (e.g., polymer and semiconductor). The channels can be formed from materials that are inherently hydrophobic or hydrophilic. Optionally, different portions of the channels can be treated to increase or decrease the channel hydrophobic or hydrophilic character (e.g., flowing polyelectrolytic polystyrene sulfonate through a PDMS channel makes the inherently hydrophobic PDMS more hydrophilic).

In embodiments of the invention where the droplets are analyzed, analysis of the droplets can be performed on-chip or off-chip, if the device is integrated into a microfluidic chip. Analysis need not be performed on-chip, such as is the case if the device is not formed as part of a chip, or if the droplets are directed off-chip. Example 1 describes both on- and off-chip analyses. Analysis of the droplets can be performed using techniques known to those of skill in the art, such as spectroscopic techniques, absorption techniques, electrochemical techniques, mass spectrometry, magnetic resonance, x-ray techniques, circular dichroism, and interfacial tension analysis. Representative analytical techniques include laser induced fluorescence (LIF), confocal fluorescence detection, single molecule fluorescence spectroscopy, two-photon fluorescence spectroscopy, multi-photon fluorescence spectroscopy, correlation spectroscopy, non-linear optical spectroscopy, second harmonic generation (SHG), sum frequency generation (SFG), third harmonic generation (THG), difference frequency generation (DFG), spontaneous parametric down conversion (SPDC), three and four wave mixing, surface enhanced Raman spectroscopy (SERS), resonance Raman spectroscopy, surface enhanced resonance Raman spectroscopy (SERRS), hyper Raman, spontaneous Raman spectroscopy, optical tweezers Raman spectroscopy (OTRS), stimulated Raman spectroscopy, spatially offset Raman spectroscopy (SORS), coherent anti-Stokes Raman spectroscopy (CARS), Raman optical activity (ROA), transmission Raman, inverse Raman spectroscopy, tip-enhanced Raman spectroscopy (TERS), atmospheric pressure chemical ionization mass spectrometry (APCI), chemical ionization mass spectrometry (CI), electron impact mass spectrometry (EI), electrospray ionization mass spectrometry (ESI), fast atom bombardment mass spectrometry (FAB), field desorption/field ionization mass spectrometry (FD/FI), matrix assisted laser desorption ionization mass spectrometry (MALDI), thermospray ionization mass spectrometry (TSP), UV/Vis, infrared spectroscopy, near infrared spectroscopy, microwave spectroscopy, cavity ring down spectroscopy (CRDS), cavity ring-down laser absorption spectroscopy (CRLAS), x-ray crystallography, nuclear magnetic resonance spectroscopy (NMR), multi-dimensional NMR, continuous wave NMR, solid-state NMR, electrochemical detection (ED), amperometry ED, conductance ED, resistive ED, and voltammetric ED.

Means for liquid delivery (e.g., pumping, or otherwise moving, liquid through channels) are known to those of skill in the art. Representative pumping means include mechanical pumps, electro-kinetic flow, syringe pumps, pneumatically-driven flow, piezoelectric-driven pumps, and pneumatically-actuated-integrated pumps.

Figure 5:
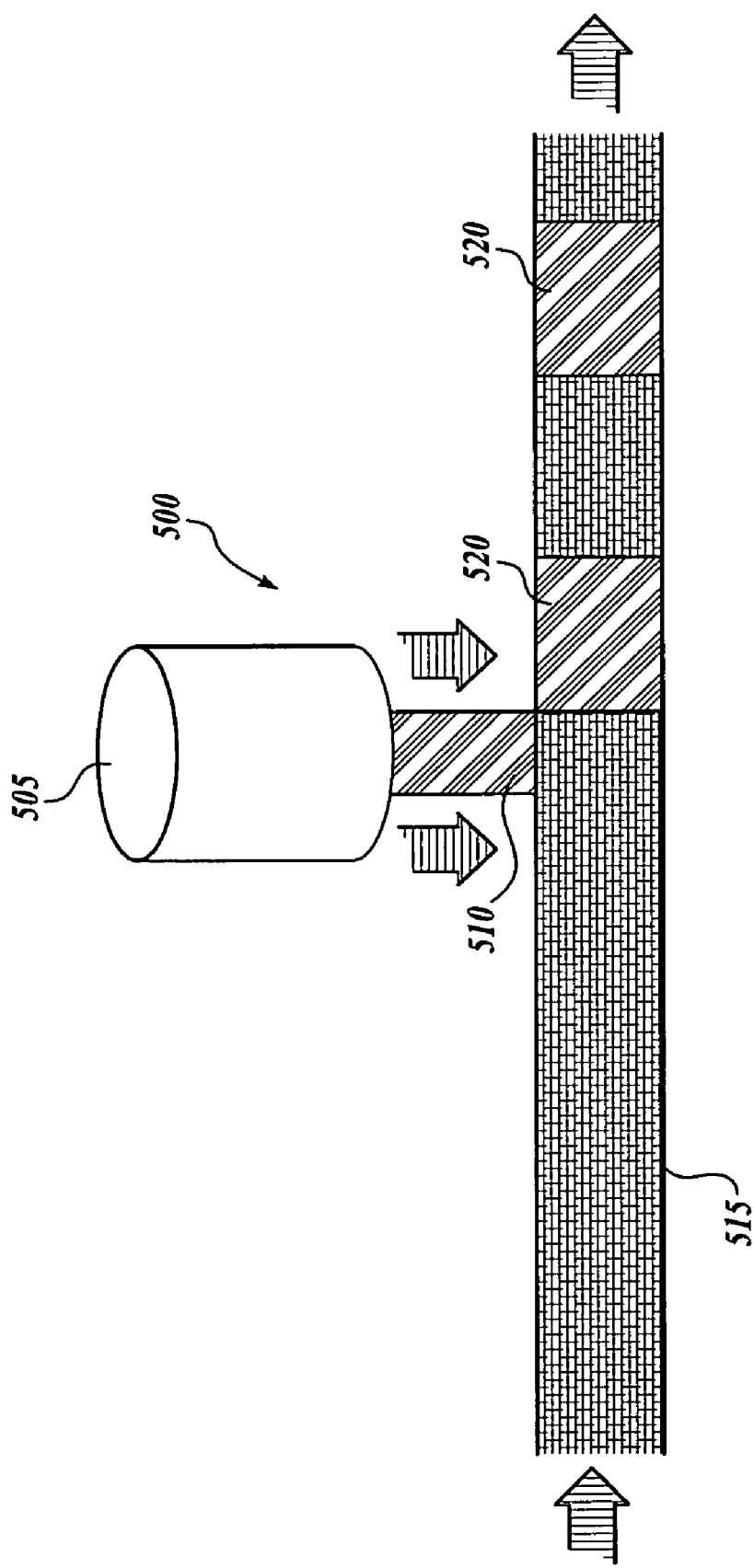
FIG. 5 illustrates a representative device of the invention for on-line sampling of a reaction through the formation of compartmentalized liquid bodies.

The invention may be better understood with reference to FIG. 1, illustrating a representative device of the invention. A carrier channel 105 transports a carrier liquid 106 through the carrier channel 105 in the direction indicated by the arrows. A sample channel 110 intersects with the carrier channel 105 at an outlet 115 of the sample channel 110, thus creating a junction. The sample channel 110 includes a sample liquid 120 that includes an analyte 121 and a buffer liquid 123. In this representative embodiment, the sample channel 110 is in fluidic communication with a separatory device (not pictured), such as a chromatographic device, which provides the sample liquid 120. For illustration purposes, analyte portions 121 are illustrated as distinct bands, yet in a separation such distinct bands may not be present and analyte concentration will vary over a length of the sample liquid 120. The carrier liquid 106 and the sample liquid 120 are immiscible, and when the sample liquid 120 is forced into the carrier liquid 106 in the carrier channel 105, a liquid body 125 is formed. The liquid bodies 125 are illustrated as droplets, but segmented plugs (as illustrated in FIG. 5) may also form if the volume of the liquid body 125 creates a cross-sectional area larger than the cross-sectional area of the transport region 130 of the carrier channel 105. A forming liquid body 116 is also illustrated.

As illustrated, liquid body 125' contains a larger concentration of analyte than liquid bodies 125, thus indicating that the separation effected by the separatory device is preserved when liquid bodies 125 and 125' are formed, and the concentration of analyte 121 is similarly preserved. Preserving the concentration of analyte 121 decreases diffusive effects that are detrimental to the integrity of post-separation analysis without the compartmentalization of the sample liquid 120 as described herein. Analyses can be performed on the liquid bodies 125 and 125' without diffusion reducing the accuracy of such analysis.

Figure 2:
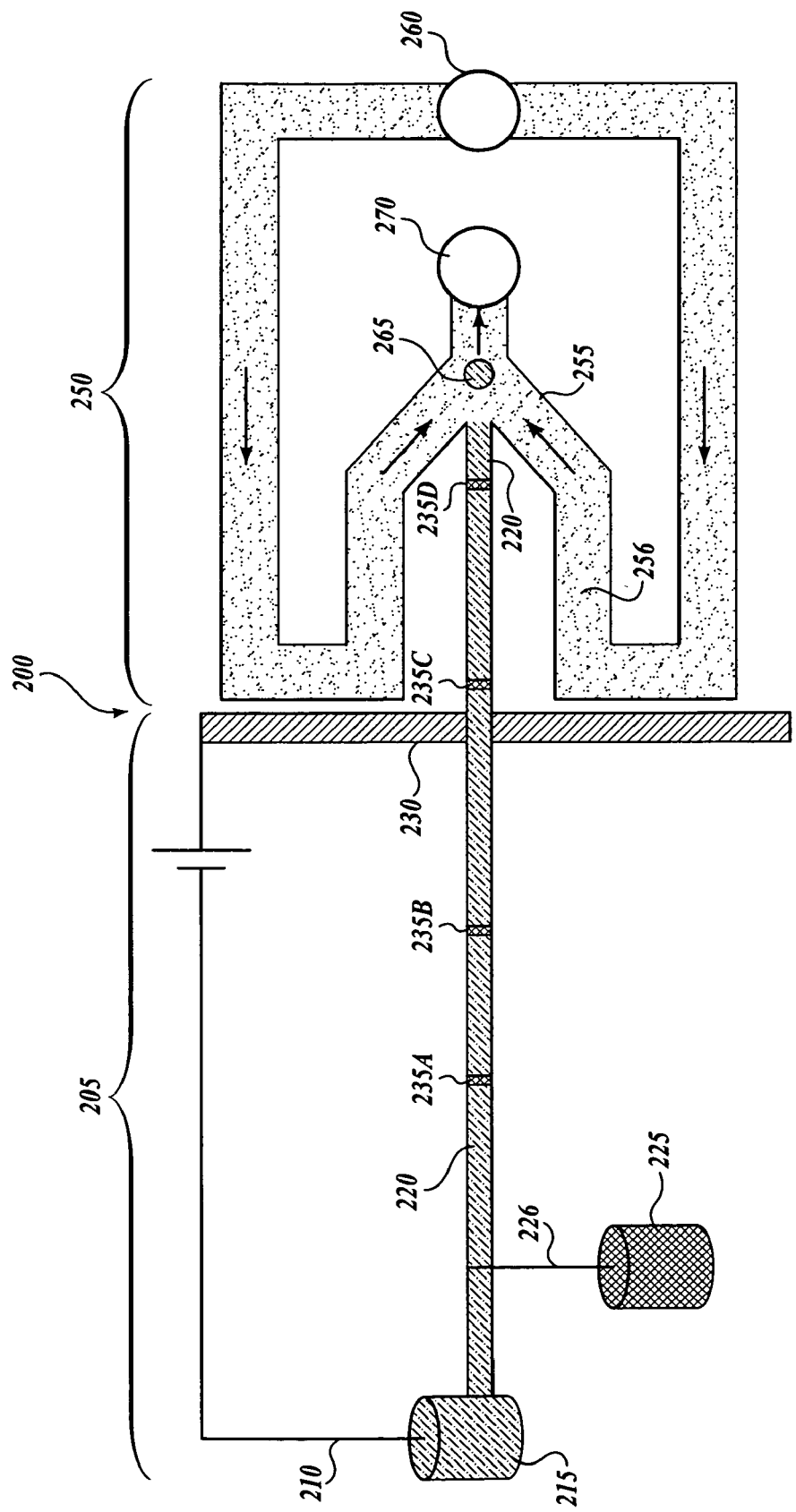
FIG. 2 illustrates a representative device of the invention integrated with a capillary electrophoresis device.

A representative device of the invention 250 integrated with a separatory device 205 is illustrated in FIG. 2, where the representative device 250 is similar to that illustrated in FIG. 1. The system 200 includes a separation device 205 that is a capillary electrophoresis device having a first electrode 210 integrated with a buffer solution 215. A channel 220 directs the buffer solution 215 through the channel 220, which is controllably with a sample solution 225 via a sample solution channel 226. The sample solution 225 is controllably released into the channel 220 via a valving mechanism (not illustrated). The combined sample solution 225 and buffer solution 215 are transported further down the channel 220 via capillary electrophoresis as a voltage is applied across the first electrode 210 and second electrode 230. Capillary electrophoresis drives the separation of the sample analyte 225 into bands 235A-D within the buffer liquid 215. Electro-osmotic flow (EOF) additionally drives the movement of the liquid in the channel 220. Thus, the sample 225 and buffer 215 are separated and moved within the channel 220 toward the droplet-forming device 250 of the invention.

In the droplet-forming device 250, the separated sample 235A-D and buffer 215 are forced into the device 250 via the sample channel 220, which intersects the carrier channel 255.

The carrier channel 255 has an immiscible carrier liquid 256 that is pushed through the carrier channel 255 by a pumping mechanism (not illustrated) feeding at an inlet 260. The device 250 as illustrated includes two branches of the carrier channel 255, fed by the inlet 260, which are directed such that flow focusing of the sample liquid 220 occurs to form a droplet 265. In the representative device 250 illustrated, the droplet 265 formed is directed toward an outlet 270 that then transports the compartmentalized, sample-containing droplet 265 to a different device for analysis, either on- or off-chip, or to a storage device for later analysis. Because of the compartmentalization effected by forming the droplet 265, the spatial and temporal nature of the sample separation by the separatory device 205 can be preserved for analysis at a later time without diffusive effects compromising the accuracy of such analyses.

Example 1 describes an exemplary device of the invention for forming droplets using CE, EOF, and device channels similar to those illustrated in FIGS. 1 and 2.

Figure 3A:
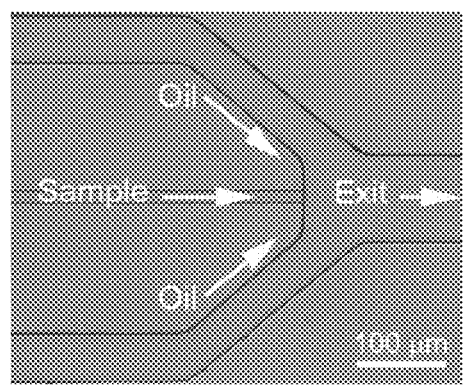
FIG. 3A is a micrograph of a representative device of the invention.
Figure 3B:
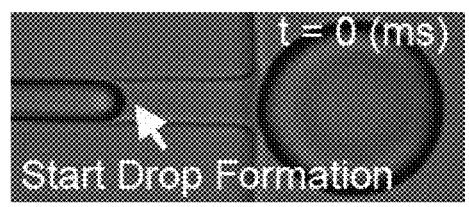
FIGS. 3B-3F are micrographs of a liquid body being formed by a representative device of the invention.
Figure 3C:
Figure 3D:
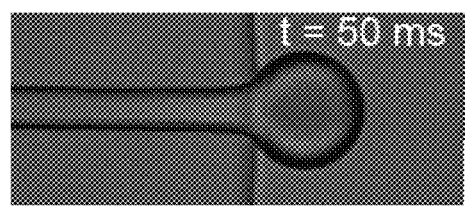
Figure 3E:
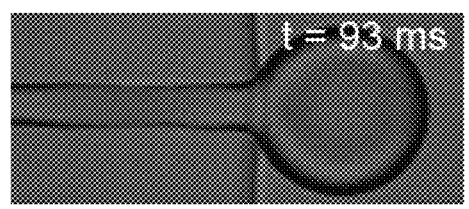
Figure 3F:
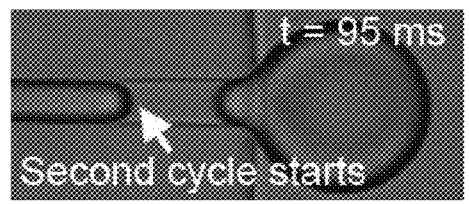

FIGS. 3A-3F illustrate an exemplary droplet-generation device in operation. FIG. 3A is a micrograph of a device formed in PDMS where an aqueous sample stream is segmented into droplets with the use of an oil stream in a flow focusing arrangement converging on the sample stream from two sides. The exit of the device directs formed droplets to be analyzed. FIGS. 3B-3F are micrographs of a timed series of images of a droplet forming at the junction between the sample stream and the oil streams of the device pictured in FIG. 3A. FIG. 3B is an image of a newly formed droplet that has detached from the sample stream. FIG. 3C is a micrograph of the sample stream approaching the interface with the oil streams. FIG. 3D is a micrograph of a droplet forming in the oil stream. FIG. 3E is a micrograph of the droplet growing in size as more sample volume flows toward the junction of the oil and sample streams. Finally, FIG. 3F is a micrograph of a formed droplet pinching off from the sample stream. Once the droplet is formed, the oil stream directs its movement.

After liquid body formation, the droplets can be transported for various analyses or operations either on or off of the fluidic chip in which the droplets are created. For some analyses, such as optical analyses, the immobilization of a droplet is required to perform the technique.

In one embodiment, analysis of droplets in a channel includes immobilizing the droplets. In a further embodiment, immobilizing the droplets in the carrier channel includes flowing the droplets past an alcove including an inlet having a size sufficient to allow a droplet to pass into the alcove and an outlet having a size insufficient to allow the droplet to pass through the outlet, such that a droplet flowing past the inlet will be preferentially directed into the alcove if there is no droplet occupying the alcove. A representative method and channel architecture for immobilizing droplets in alcoves at T-junctions of fluidic channels is described in Shi et al., "Droplet-based microfluidic system for individual *Caenorhabditis elegans* assay" *Lab Chip*, 2008, 8, 1432-1435, incorporated herein by reference in its entirety.

Figure 4A:
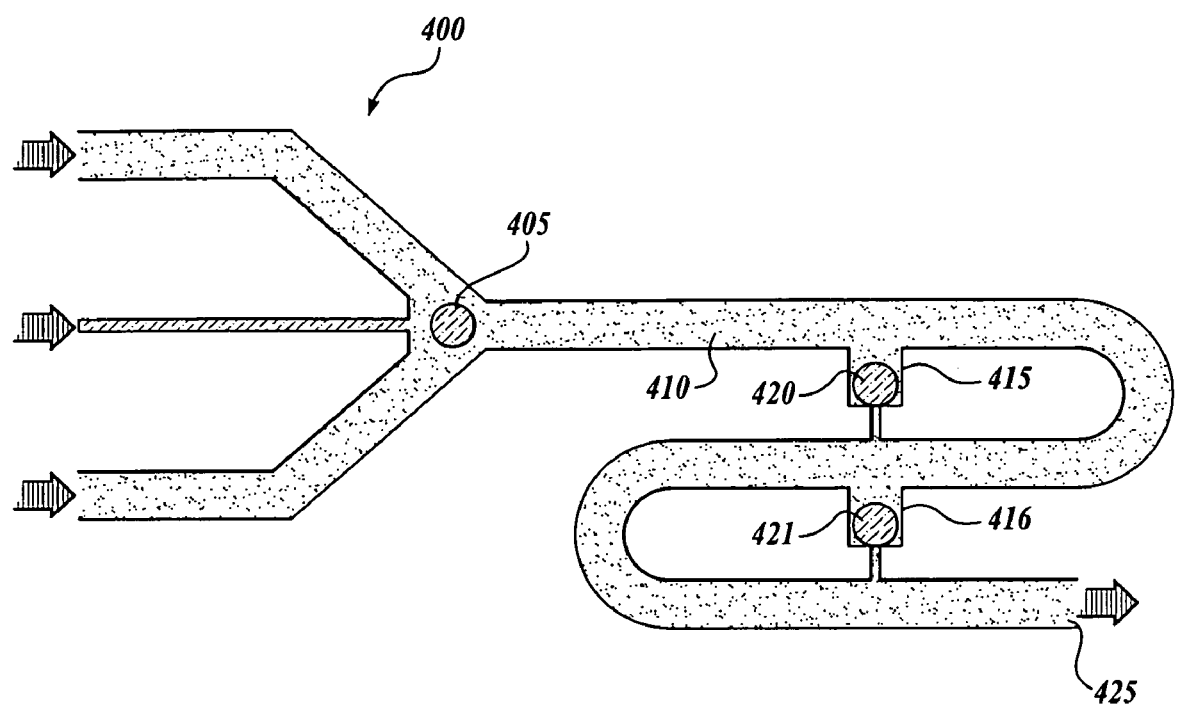
FIGS. 4A-4D are diagrammatic illustrations of a representative device of the invention that includes the formation of liquid bodies and alcoves for trapping the liquid bodies for analysis.

Alcoves for immobilizing droplets are diagrammatically illustrated in FIGS. 4A-4D, and Example 2 describes experimental results obtained with devices having alcoves for immobilizing and analyzing droplets. FIG. 4A illustrates a diagrammatic view of a droplet-forming device 400 of the invention, including an outlet channel 410 with alcoves 415 and 416. A droplet 405 is formed and moved along the outlet channel 410 toward a first alcove 415. As illustrated in FIG. 4A, the outlet channel 410 is a serpentine channel containing several alcoves 415, 416 and continues on toward further components of the fluidic system or to an outlet for the system. In the device of FIG. 4A, two droplets 420, 421 are illustrated as immobilized ("docked") in alcoves 415, 416, respectively. Because the alcoves 415, 416 are filled with droplets 420, 421, the recently formed droplet 405 would be transported past the alcoves and toward the outlet 425. The filling of the alcoves 415, 416 with droplets 420, 421 is further described with reference to FIGS. 4B-4D.

Figure 4B:
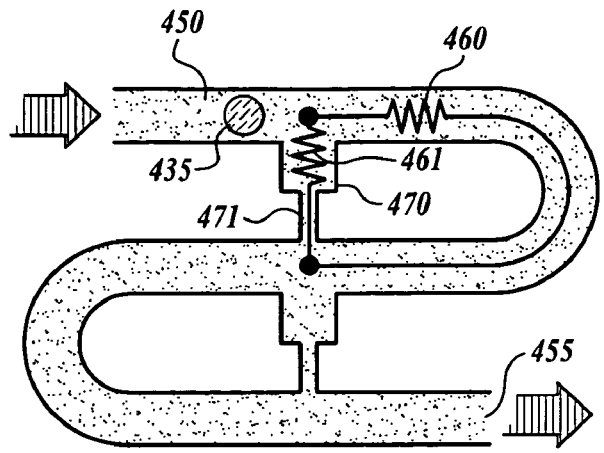
Figure 4C:
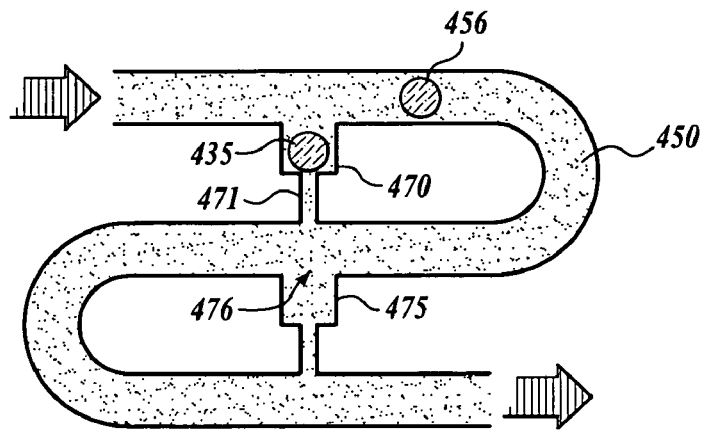
Figure 4D:
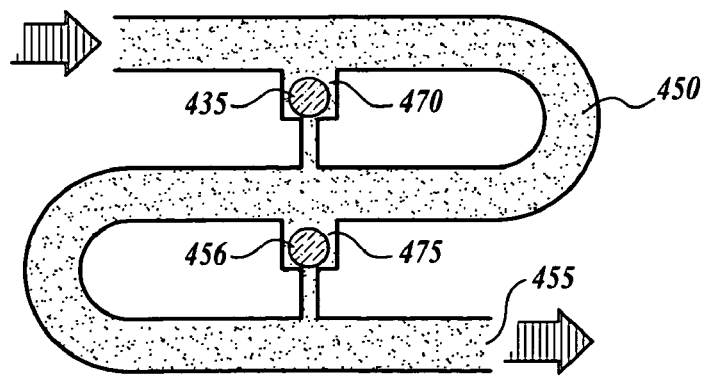

FIG. 4B illustrates a serpentine channel 450. A droplet 435 is positioned flowing toward the outlet 455 of the channel 450. In the diagrammatic illustration of FIG. 4B, two resistive icons 460, 461 represent the fluidic resistivity at the illustrated portions of the channel 450. When no droplet 435 is present in the first alcove 470, the resistance 461 is less than resistance 460, and the droplet 435 is directed down the first alcove channel 471 preferably. When the droplet 435 reaches the junction between the alcove 470 and the channel 450, the smaller resistivity 461 preferentially directs the droplet 435 into the alcove 470, as illustrated in FIG. 4C. In FIG. 4C, the first droplet 435 is situated within the first alcove 470. When a single droplet 435 is situated within the alcove 470, the alcove channel 471 is blocked, and the flow resistance 461 through the channel is greatly increased such that a second droplet 456 trailing the first droplet 435 will be preferentially directed past the first alcove 470 and further down the channel 450 toward a second alcove 475. Upon reaching the junction 476 between the second alcove 475 and the main channel 450, the second droplet 456 is preferentially directed into the second alcove 475 by the same resistance-based selection as occurred with the first droplet 435 in the first alcove 470. The second droplet 456 situates within the second alcove 475, as illustrated in FIG. 4D. Further droplets would travel past the first alcove 470 and second alcove 475 and toward the outlet 455.

As described in Example 2, once the droplets (e.g., 435 and 456) are immobilized in the alcoves (470, 475), analytical techniques can be performed on the droplets, and the sequential nature of droplet formation can be further preserved during the docking process described because the droplets are docked in the sequential order in which they arrive at the alcoves. Thus, in a particular section of channel, the first droplet to reach the section of channel will be deposited in the first alcove, the second droplet will be deposited in the second alcove, and so on.

The use of the described methods and devices for preserving the separation of an analyte-containing solution from a separatory device is a preferred embodiment of the invention. The on-line sampling of an ongoing reaction, to monitor the progress of such a reaction, is an additional application for which the methods and devices are useful. The term "on-line sampling" refers to a sample extracted from an ongoing or completed reaction. Representative reactions include a chemical reaction in a reaction vessel or a biological process in a bioreactor. The purpose of such on-line sampling is to determine the composition of the reaction vessel at a specific point in time, so as to track the transformation of the contents of the reaction from an initial state to a final state. In a chemical reaction, the initial reactants are added to a reaction vessel and the formation of a product is not instantaneous, but is typically a process that lasts minutes, hours, or days as reactants react to form the product. On-line sampling can be used to extract a small volume of the reacting mixture and to determine the composition of the contents of the reaction vessel at the specific time of the extraction. Several extractions at several different reaction times will give a profile of the progression of the reaction and can be used to determine the mechanism by which the reaction is occurring based on the relationship between temporal and physical reaction characteristics.

In another aspect, a method is provided for preserving a liquid stream of an on-line sample of a reaction in a reaction vessel. In one embodiment, the method includes flowing a carrier liquid through a carrier channel to provide a carrier liquid stream and introducing a sample liquid, immiscible with the carrier liquid, through a sample channel into the carrier liquid stream at a rate sufficient to provide segmented liquid bodies of the sample liquid in the carrier liquid stream, the sample liquid including a stream of liquid extracted from a reaction vessel, the sample stream further including an analyte.

In another aspect, a device is provided for preserving a liquid stream of an on-line sample of a reaction in a reaction vessel. In one embodiment, the device includes a carrier channel having an inlet and an outlet; a carrier liquid reservoir in liquid communication with the carrier channel inlet; a carrier liquid delivery means for delivering a carrier liquid from the carrier liquid reservoir to the carrier channel inlet at a first flow rate; a sample channel having an inlet and an outlet, wherein the sample channel outlet intersects the carrier channel intermediate the carrier channel inlet and carrier channel outlet; a reaction vessel in liquid communication with the sample channel inlet; and a sample liquid delivery means for delivering a sample liquid from the reaction vessel to the sample channel outlet at a second flow rate; where the first flow rate and the second flow rate are sufficient to form a liquid body of the sample liquid at the outlet of the sample channel.

Similar to the above-described difficulties with preserving the effluent from a separatory device due to diffusive effects, an on-line sample will diffuse and lose the accuracy of its sampling time as the sample volume is transported away from the reaction vessel and toward an analytical device. By directing the sampled liquid from a reaction vessel into a device of the invention and forming compartmentalized liquid bodies of the sampled liquid, the temporal nature of the on-line sample can be preserved and diffusive effects minimized. Compartmentalization of a liquid on-line sample in an immiscible fluid is also beneficial because it can minimize cross-contamination by preventing direct sample contact with the channel (e.g., when the droplets are separated from the channel wall by the carrier liquid). Once the sample is in droplet form, the droplets can be transported to an analytical device for analysis.

The elimination of diffusion and dispersion by encapsulation of the sample liquid in the carrier liquid stream allows for high sensitivity analysis by preserving the analyte concentration. Furthermore, sensitive analyses can be performed with high fidelity due to the minimization of cross-contamination of the encapsulated analytes. This method provides high time resolution due to the high throughput and short duty cycle of the encapsulation process.

FIG. 5 diagrammatically illustrates an on-line sampling device 500 of the invention. The on-line sampling device directs a sample of reactant from a reaction vessel 505 into a sample channel 510. The sample channel 510 intersects with a carrier channel 515 in a T-junction, and segmented liquid plugs 520 are formed in a manner similar to that described above for forming liquid bodies from chemically-separated fluid streams. The reaction occurring in the reaction vessel 505 can be sampled at a given time during the course of the reaction, and the temporal nature of such a sampling is preserved by forming liquid plugs 520 of the sampled reaction.

The devices of the invention are a useful addition to a chemical-separation system (e.g., an HPLC system). Thus, in another aspect, a chemical separation system is provided. In one embodiment, the chemical separation system includes a chemical-separation device configured to separate a liquid mixture into at least two components. The chemical separation device includes a device outlet producing a separated liquid mixture effluent stream, where the device outlet is in liquid communication with a device for preserving the separation integrity of the separated liquid mixture effluent stream. The device for preserving the separation integrity of the separated liquid mixture effluent stream includes a carrier channel having an inlet and an outlet; a carrier liquid reservoir in liquid communication with the carrier channel inlet; a carrier liquid delivery means for delivering a carrier liquid from the carrier liquid reservoir to the carrier channel inlet at a first flow rate; a sample channel having an inlet and an outlet, where the sample channel outlet intersects the carrier channel intermediate the carrier channel inlet and carrier channel outlet; and a sample liquid delivery means for delivering the separated liquid mixture effluent stream from the chemical-separation device outlet to the sample channel inlet at a second flow rate. The first flow rate and the second flow rate are sufficient to form a liquid body of the separated liquid effluent stream at the outlet of the sample channel.

In another aspect, a method for preventing diffusion in a liquid stream is provided, the method including flowing a carrier liquid through a carrier channel to provide a carrier liquid stream; and introducing a sample liquid portion of a sample liquid, immiscible with the carrier liquid, through a sample channel into the carrier liquid stream at a rate sufficient to provide a segmented liquid body of the sample liquid portion in the carrier liquid stream, the sample liquid portion including an analyte having a concentration defined in the sample liquid stream related to the time at which the sample liquid portion was formed.

The following examples are provided for the purpose of illustrating, not limiting, the invention.

EXAMPLES

General Procedures

Microfluidic droplet-forming devices were fabricated with SU-8 negative photoresist mold on three-inch polished silicon wafers using standard photolithography techniques. A device was cast using polydimethylsiloxane (PDMS), and after treatment with oxygen plasma, was bonded to PDMS-coated microscope slides. Freshly oxidized PDMS is hydrophilic; therefore to promote droplet generation, the device was allowed to bake for a minimum of 24 hours in a 120° C. oven to revert the surface of the PDMS channel back to its hydrophobic state. Prior to running the device, the polyelectrolyte polystyrene sulfonate (PSS) was flowed through the separation channel by a syringe pump to make the separation channel hydrophilic, allowing for more efficient EOF than in native PDMS, while leaving the oil and exit channels hydrophobic to prevent droplet wetting.

ITO coated slides (CG-90IN-S210) from Delta Technologies (Stillwater, Minn.) were masked with Kapton silicone adhesive tape from Kaptontape.com (Torrance, Calif.) before being developed in an etchant solution consisting of 20% HCl and 5% $HNO_3$. This procedure removed the ITO from the unmasked region of the chip, leaving a ~1 mm electrode under the tape. The tape was left on the chip while a mixture of PDMS (2-part PDMS prepolymer/1 part catalyst) was spun coated onto the microscope slide.

To generate droplets with EOF, it was necessary to balance the fluidic pressure at the aqueous-oil interface, which was achieved with the use of a homemade fluidic actuator comprised of a syringe attached to a micrometer to allow for sensitive pressure control of the interface. The platinum electrode, through which high voltage was delivered, was placed in the tubing connected to the syringe so that the electrode was inserted with the tubing into the buffer reservoir. This technique allowed the placement of the electrode directly at the buffer-reservoir end of the separation channel.

For CE separation, a mixture of fluorescein isothiocyanate (FITC) labeled amino acids was used. For the second-dimension analysis, MEKC separation of D/L glutamate, droplets containing the D/L glutamate band into a 10 µm inner-diameter fused silica capillary (Polymicro Technologies, Phoenix, Ariz.) were injected. The capillary was mounted on a high-resolution micromanipulator from Narishige (MHW-3; Eastmeadow, N.Y.) and the droplet contents were injected into the capillary by contacting the tip of the capillary with the droplets. After injection, the capillary was placed in a buffer solution containing 20 mM borate, 30 mM sodium dodecyl sulfate, and 20 mM of β-cyclodextrin, at pH 9 and a 250 V/cm field was applied.

For confocal detection, the output of a 488 nm diode laser (Sapphire CDRH LP; Coherent, Santa Clara, Calif.) was directed into a Nikon TE2000 microscope (Melville, N.Y.), where the beam was reflected off a dichroic mirror (488/1064 pc; Chroma, Rockingham, Vt.), and focused into the microchannel through a Nikon 20× objective (0.40 NA). The emitted fluorescence was spectrally filtered through a bandpass filter (HQ550/100; Chroma), then passed through a 100 µm pinhole placed at the image plane, and detected with an avalanche photodiode (SPCM-AQR-12; Perkin Elmer, Waltham, Mass.). For uncaging experiments, a cylindrical lens was used to shape the 355 nm output from a frequency-tripled Nd:YAG laser, such that the resulting line was focused into a ~2 µm wide line by a Nikon 20× (0.75 NA) Super Fluor objective.

CMNB caged-fluorescein (fluorescein bis-(5-carboxymethoxy-2-nitrobenzyl)ether (F-7103) was purchased from Invitrogen (Carlsbad, Calif.). Fluorescein isothiocyanate and sodium dodecyl sulfate were obtained from EMD Biosciences (Darmstadt, Germany). Amino-acids (phenylalanine, glycine, D-glutamate, and L-glutamate), β-cylcodextran, AR20 silicone oil, and poly(styrenesulfonate) were purchased from Sigma-Aldrich, (St. Louis, Mo.). FC-40 Fluorinert was obtained from 3M (St. Paul, Minn.).

Example 1

Droplet Formation and Analysis of Liquid Separated by Capillary Electrophoresis

A fluidic-device design similar to that illustrated in FIG. 2 was used to compartmentalize CE-separated bands of analyte. The device was fabricated in polydimethylsiloxane (PDMS) and consisted of three regions: (1) a sample injection region, (2) a CE separation channel, and (3) a droplet formation region. The sample-injection channel was 3 µm by 3 µm cross-section and served as a fluidic resistor between the sample reservoir and the CE separation channel. Injection of a sample plug into the CE channel was achieved using a "screw valve" to press down on the sample-injection channel. The screw was "closed" (i.e., pressed down to block off the channel) before and after injection, thus the pressure remained balanced and the sample solution was unable to bleed into the separation channel during CE.

The CE channel cross-section was 10 µm×10 µm. The droplet formation region was comprised of two oil channels (50 µm×50 µm in cross-section) that flanked the CE channel and an exit channel that was 50 µm tall by 100 µm wide. The CE channel has a smaller cross-section than the exit channel to prevent flow from the oil channel into the CE channel. EOF in the CE channel was initiated by applying a high voltage to the platinum (Pt) electrode and by grounding the indium tin oxide (ITO) electrode on the floor of the microchannel. In the absence of applied voltage, the aqueous-oil interface was balanced and no droplet formation occurred.

Figure 6A:
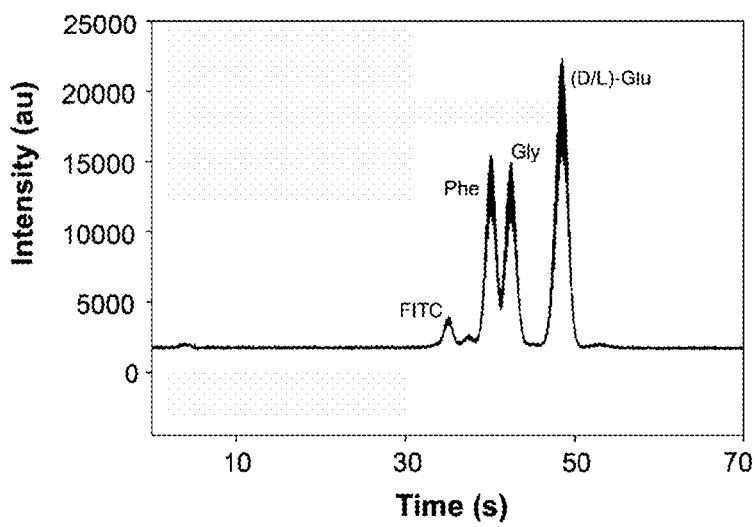
FIGS. 6A-6C are electropherograms of data acquired at various locations within a representative device of the invention separating a mixture of amino acids.
Figure 6B:
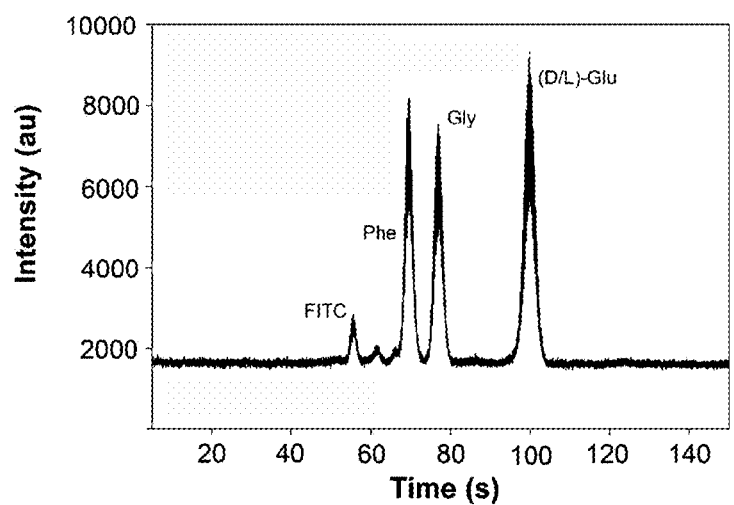
Figure 6C:
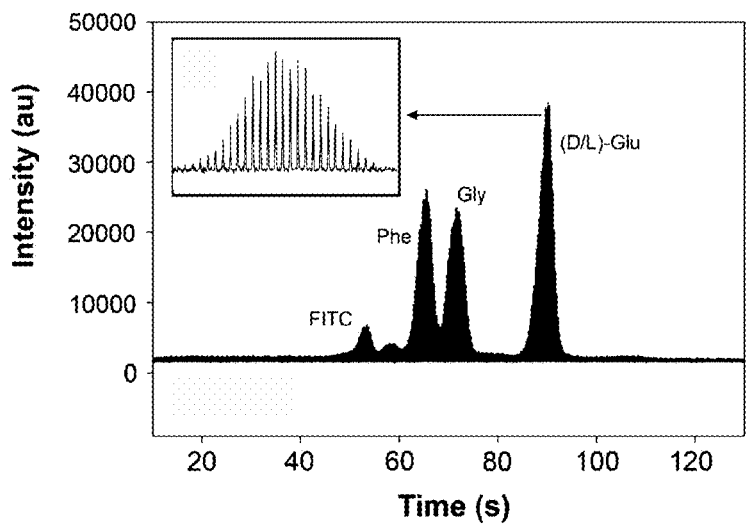

To characterize the effect of droplet formation on CE separation, the separated bands at three locations were monitored: (1) in the CE channel during separation, (2) immediately before droplet formation, and (3) after droplet formation. FIGS. 6A-6C show the separated CE peaks at each of these three detection spots, respectively. FIG. 6A is an electropherogram recorded at the detection location in the CE channel, which shows all amino acids were separated by CE except for D and L glutamate.

FIG. 6B is an electropherogram recorded at the second detection spot, prior to droplet formation.

FIG. 6C is an electropherogram recorded at the third detection spot, after the droplet-formation region. Expansion of the D/L glutamate peak (inset) reveals many individual peaks. Here, each peak contained within the Gaussian envelope of the D/L glutamate peak is a droplet, and the detected fluorescence signal drops back to the baseline level between each droplet.

Figure 7A:
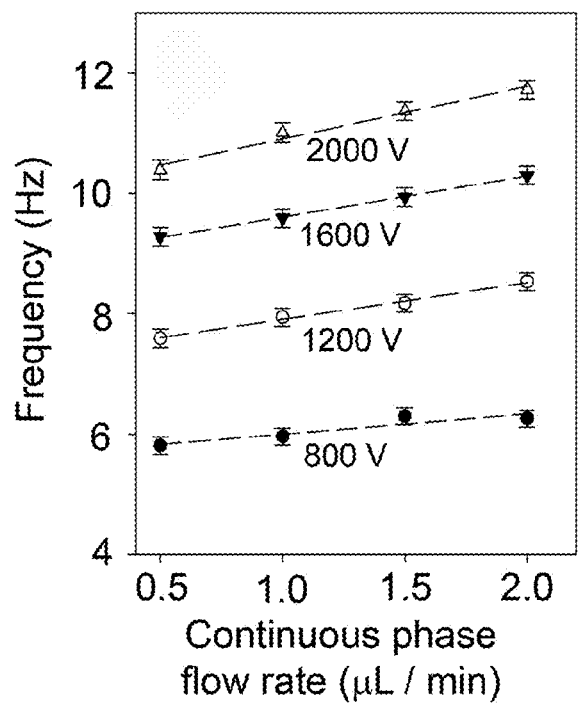
FIGS. 7A and 7B are graphs illustrating experimental data related to the frequency (FIG. 7A) and volume (FIG. 7B) of liquid bodies generated in representative devices of the invention.
Figure 7B:
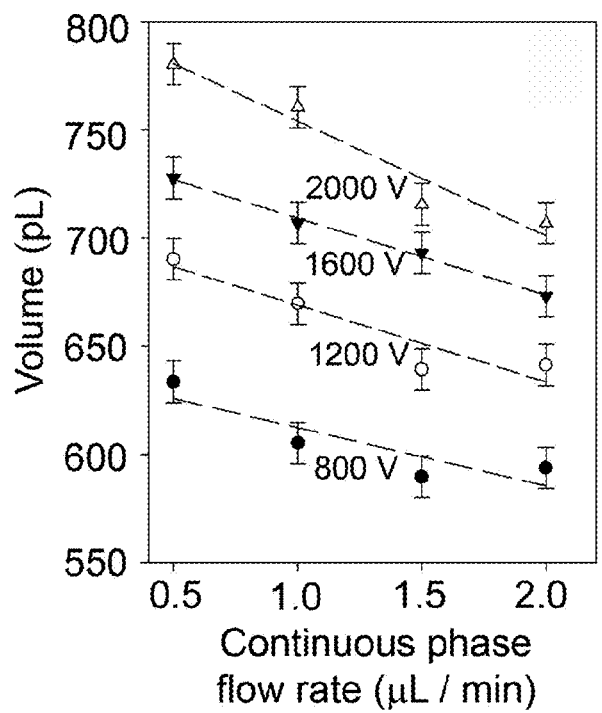

The frequency and size of the droplets formed depends both on the strength of the applied electric field and the flow rate of the continuous immiscible phase, as illustrated in FIGS. 7A and 7B. At a given continuous-phase flow rate, higher voltages increased the EOF rate and thus increased both the rate and volume at which the droplets were generated. For a given applied field strength, increasing the continuous-phase flow rate increased the frequency of droplet generation (FIG. 7A) but decreased the volume of the droplet formed (FIG. 7B). At a given field strength, the EOF rate is constant, and thus the volume of each droplet must decrease to support the higher frequency of droplet formation.

Figure 8A:
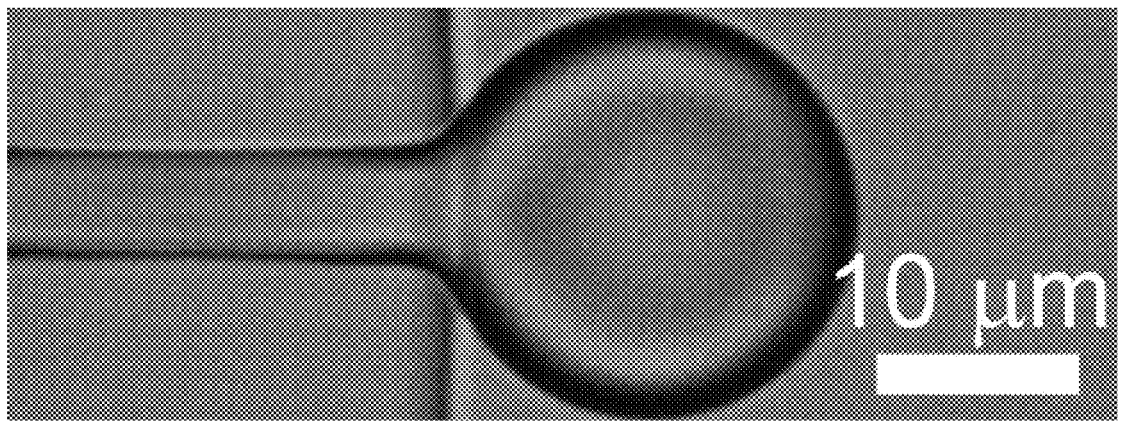
FIGS. 8A and 8B are micrographs of liquid bodies formed by representative devices in carrier liquids having different chemical compositions.
Figure 8B:
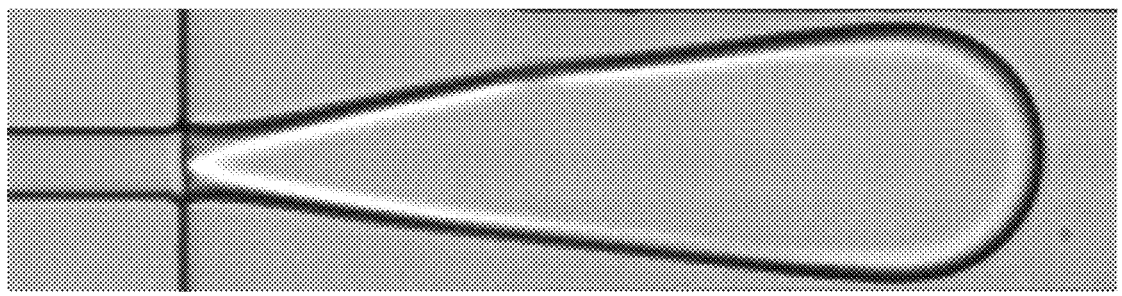

In addition to applied voltage and continuous-phase flow rate, the frequency and size of droplets formed can be tuned over a wide range using different immiscible fluids. For example, under identical operating conditions, the frequency and volume at which aqueous droplets were formed was 10 Hz and 0.3 nL in a silicone oil (FIG. 8A), but changed to 0.3 Hz and 1 nL when a fluorinated liquid was used (FIG. 8B).

Additionally, off-chip analysis was performed by transferring the contents of droplets containing D/L glutamate into a fused silica capillary for a second dimension separation using micellular electrokinetic chromatography (MEKC). The injection of the D/L glutamate-containing droplets into the capillary was achieved by positioning the tip of the capillary onto the droplets, which, upon contact with the hydrophilic surface of the capillary, wetted and entered the capillary. The capillary was mounted on a high-resolution micromanipulator to facilitate fine positional control. After injection, the tip of the capillary was immersed into a vial containing the separation buffer, and a high voltage was applied across the capillary to initiate separation. The second-dimension MEKC separation and analysis confirmed the identity of the D/L peak.

The dynamics of EOF droplet formation was also analyzed. Most traditional microfluidic methods for continuous-stream droplet generation rely on either a T-channel or flow-focusing geometry. The device of this Example utilizes a modified flow-focusing design in which droplet generation is driven by EOF. Because EOF can be switched on and off in microseconds, the device has the potential to generate droplets of varying spatial frequencies rather than a continuous stream of evenly spaced droplets. For EOF-induced droplet generation, the maximum absolute pressure ($\Delta P_{max}$) generated by EOF can be estimated for the CE channel with the relationship: $\Delta P_{max} = 32\epsilon_0\epsilon_r\zeta U w^{-2}$. Here $\epsilon_0$ is the electrical permittivity of vacuum, $\epsilon_r$ is the relative permittivity of the medium, $\zeta$ is the zeta potential of the PDMS channel wall, U is the applied voltage, and w is the width of the channel. Using literature values of $8.85 \times 10^{-12}$ $C^2N^{-1}m^{-2}$ for $\epsilon_0$, 80 for $\epsilon_r$, and $-50$ mV for $\zeta$, and using the values of U (1 kV) and w (10 μm) from the experimental device, $\Delta P_{max}$ is about 1.6 psi. This value is comparable to the hydrodynamic pressure that has been reported to produce droplets in the frequency range of kHz in a standard flow-focusing device.

Example 2

Droplet Immobilization

Depending on the application, droplets might be further analyzed on-chip or removed off-chip for additional separation or assay. For further on-chip analysis, optical and electrochemical techniques are typically useful for analysis, but for these techniques the droplets need to be docked and stored in a spatially defined manner after chemical separation. Droplets were generated in this experiment with a device similar to that of FIG. 2.

Figure 9A:
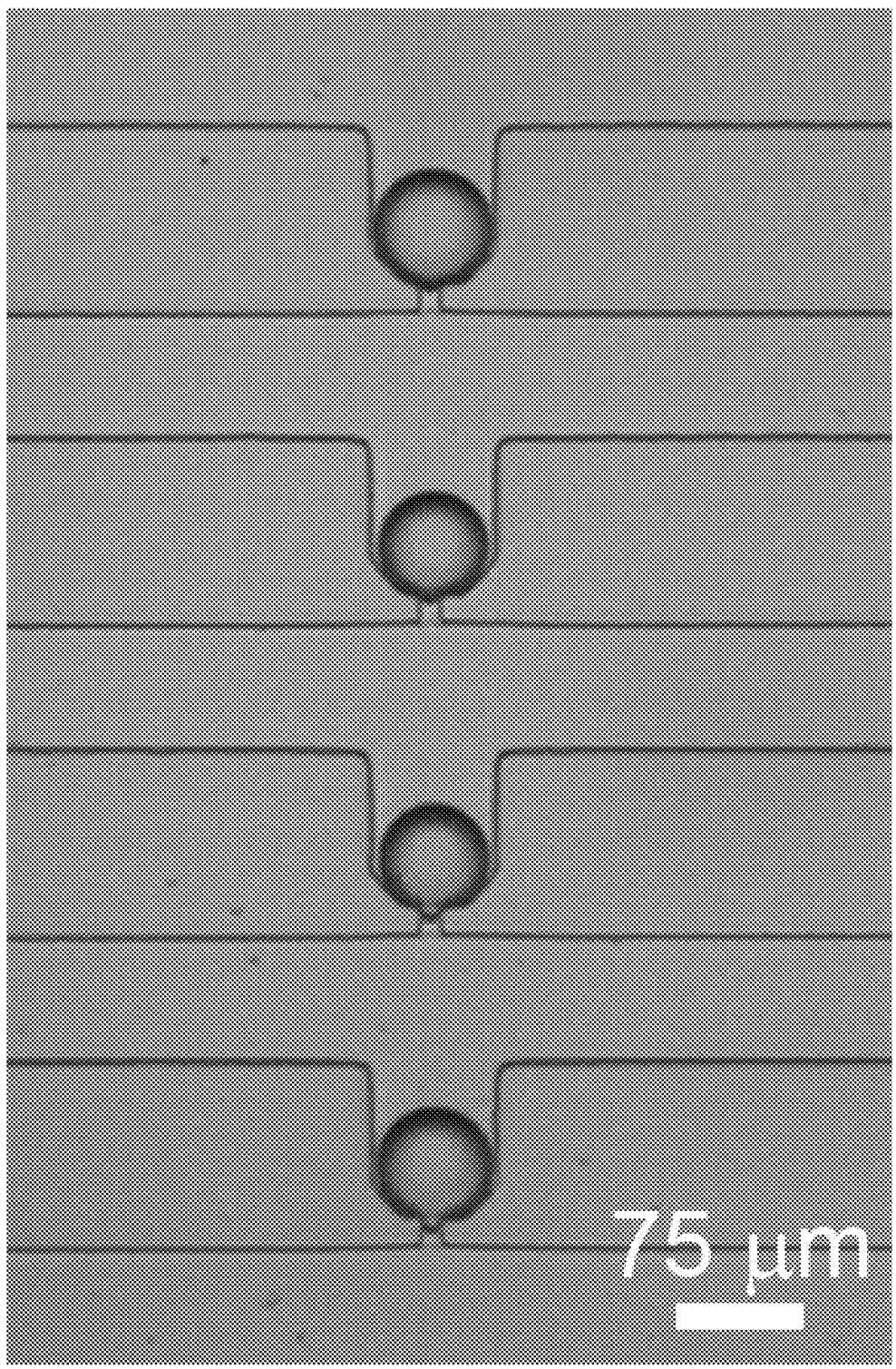
FIGS. 9A and 9B are micrographs of liquid bodies immobilized in alcoves of representative devices of the invention.

To facilitate docking of droplets, a device was fabricated similar to the device of FIG. 4A with tall and wide channels with alcoves (50 μm×75 μm), where droplets flowed and docked, and small constricted channels (10 μm×10 μm), that allowed for liquid flow through the alcoves but which prevented the droplets from passing through, as illustrated in FIG. 9A. In the absence of droplets, the flow path through the small constricted channel offers less flow resistance than the path down the larger channel. As a result, a droplet flows and becomes docked because it cannot pass through the small constricted channel. The presence of the docked droplet increases the flow resistance in the small channel and thus prevents the next droplet from being docked at the same site. Therefore, the order by which the droplets left a CE channel is encoded in their docking positions, with the first droplet leaving the CE channel being docked first and the last droplet being docked at the end of the large channel. FIG. 9A shows a series of droplets docked in this manner. Because droplets are deformable, it is important to apply a lower fluidic pressure than that required to deform the droplets and force them through the constriction. This is a useful feature for some applications, however, as it permits the use of high pressure to clear the docking sites such that the device can be re-used.

Figure 9B:
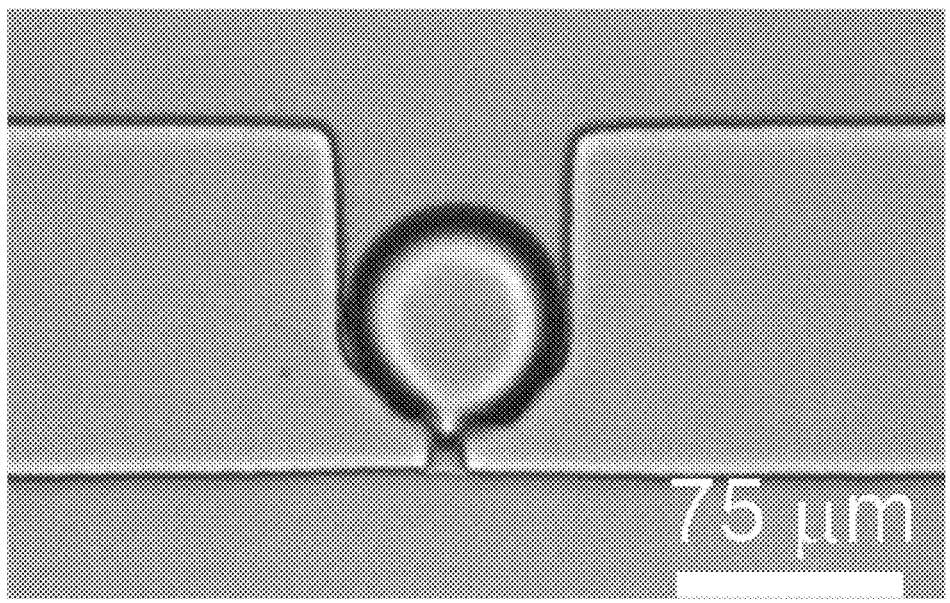
Figure 9C:
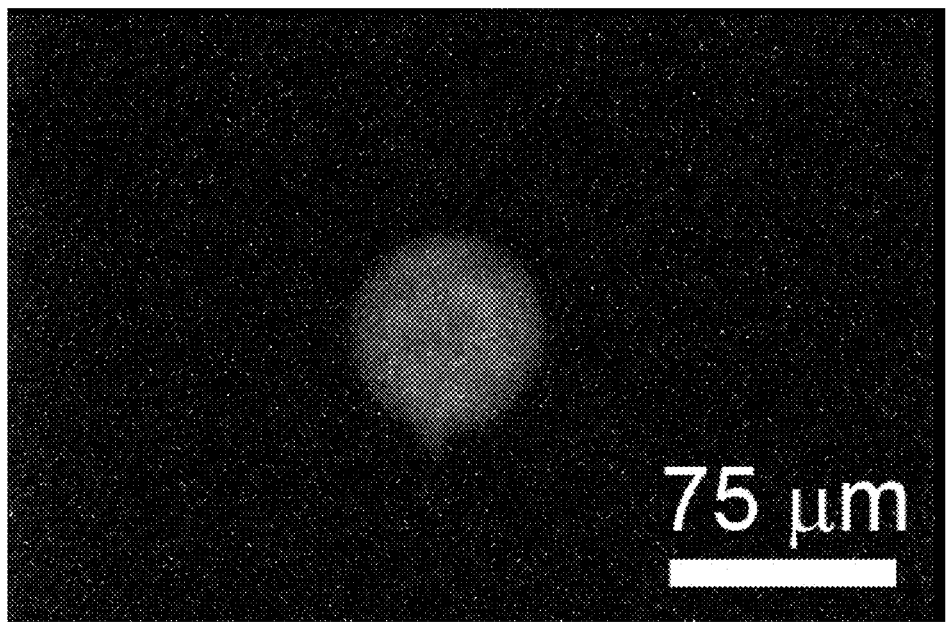
FIG. 9C is a fluorescence micrograph of the liquid body pictured in FIG. 9B.

To illustrate the use of droplet-docking for trapping a desired band in the CE channel, a cylindrically-focused UV laser pulse (3 ns at 355 nm) was used to uncage a sharp band (~2 μm wide) of caged fluorescein, similar to established procedures used for optically gated injection. This band was then transported down the CE channel by EOF, encapsulated in a droplet, then docked in the serpentine channel as illustrated in FIG. 9B. Fluorescence imaging confirmed the presence of fluorescein in the droplet, as illustrated in FIG. 9C.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for preserving the separation integrity of a chemically-separated liquid stream using a device comprising a sample channel having a proximal end and a distal end, said proximal end comprising a reservoir of buffer solution, and said distal end opening into a carrier channel, the method comprising:

(a) flowing a carrier liquid through the carrier channel to provide a carrier liquid stream; and (b) introducing a sample liquid, immiscible with the carrier liquid, through the sample channel into the carrier liquid stream at a rate sufficient to provide segmented liquid bodies of the sample liquid in the carrier liquid stream, the sample liquid comprising the effluent of a separatory device, the effluent comprising an analyte:

wherein the carrier channel has a single carrier inlet in upstream liquid communication with a first branch and a second branch, the first and second branches intersecting at a junction of the sample channel where the sample liquid is introduced into the carrier liquid stream, wherein the sample channel and the junction of the sample channel define an axis and the first and second branches intersect the axis at non-perpendicular angles; and wherein providing segmented liquid bodies of the sample liquid in the carrier liquid stream comprises simultaneously flowing the carrier liquid from the carrier inlet, through the first branch and the second branch of the carrier channel, towards the junction of the sample channel while the sample liquid is introduced into the carrier channel through the junction.

2. The method of claim 1, wherein the carrier channel cross-sectional area is larger than the sample channel cross-sectional area.

3. The method of claim 1 further comprising analyzing the segmented liquid bodies to detect the analyte.

4. The method of claim 3, wherein analyzing the segmented liquid bodies comprises a technique selected from the group consisting of spectroscopic techniques, absorption techniques, electrochemical techniques, mass spectrometry, magnetic resonance, x-ray techniques, circular dichroism, and interfacial tension analysis.

5. The method of claim 3, wherein analyzing the segmented liquid bodies comprises analyzing the droplet in the carrier channel.

6. The method of claim 5, wherein analyzing the segmented liquid bodies in the carrier channel comprises immobilizing the segmented liquid bodies in the carrier channel.

7. The method of claim 6, wherein immobilizing the segmented liquid bodies in the carrier channel comprises flowing the segmented liquid bodies past an alcove comprising an inlet having a size sufficient to allow a liquid body to pass into the alcove and an outlet having a size insufficient to allow the liquid body to pass through the outlet, such that a first liquid body flowing past the inlet will be preferentially directed into the alcove if there is no liquid body occupying the alcove.

8. The method of claim 1, wherein the carrier liquid is a non-polar liquid and the sample liquid is a polar liquid.

9. The method of claim 1, wherein the separatory device is selected from the group consisting of a chromatographic device and an electrokinetic device.

10. The method of claim 1, wherein the separatory device is selected from the group consisting of a high-performance liquid chromatography device and a capillary electrophoresis device.

11. A method for preserving the separation integrity of a chemically-separated liquid stream using a device comprising a sample channel having a proximal end and a distal end, said proximal end comprising a reservoir of buffer solution, and said distal end opening into a carrier channel, the method comprising:
  (a) flowing a carrier liquid through the carrier channel to provide a carrier liquid stream; and
  (b) introducing a sample liquid, immiscible with the carrier liquid, through the sample channel into the carrier liquid stream at a rate sufficient to provide segmented liquid bodies of the sample liquid in the carrier liquid stream, the sample liquid comprising the effluent of a separatory device, the effluent comprising an analyte;
  wherein introducing the sample liquid into the carrier liquid stream comprises using electroosmotic flow to move the sample liquid through the sample channel by applying a voltage across a first electrode, disposed at the proximal end of the sample channel, and a second electrode that transverses the sample channel and is disposed intermediate the proximal end and the distal end of the sample channel;
  wherein the carrier channel has a single carrier inlet in upstream liquid communication with a first branch and a second branch, the first and second branches intersecting at a junction of the sample channel where the sample liquid is introduced into the carrier liquid stream, wherein the sample channel and the junction of the sample channel define an axis and the first and second branches intersect the axis at non-perpendicular angles; and
  wherein providing segmented liquid bodies of the sample liquid in the carrier liquid stream comprises simultaneously flowing the carrier liquid from the carrier inlet, through the first branch and the second branch of the carrier channel, towards the junction of the sample channel while the sample liquid is introduced into the carrier channel through the junction.

12. A method for preserving a liquid stream of an on-line sample of a reaction in a reaction vessel using a device comprising a sample channel having a proximal end and a distal end, said proximal end comprising a reservoir of buffer solution, and said distal end opening into a carrier channel, the method comprising:
  (a) flowing a carrier liquid through the carrier channel to provide a carrier liquid stream; and
  (b) introducing a sample liquid, immiscible with the carrier liquid, through the sample channel into the carrier liquid stream at a rate sufficient to provide segmented liquid bodies of the sample liquid in the carrier liquid stream, the sample liquid comprising a stream of liquid extracted from a reaction vessel, the sample stream further comprising an analyte;
  wherein the carrier channel has a single carrier inlet in upstream liquid communication with a first branch and a second branch, the first and second branches intersecting at a junction of the sample channel where the sample liquid is introduced into the carrier liquid stream, wherein the sample channel and the junction of the sample channel define an axis and the first and second branches intersect the axis at non-perpendicular angles; and
  wherein providing segmented liquid bodies of the sample liquid in the carrier liquid stream comprises simultaneously flowing the carrier liquid from the carrier inlet, through the first branch and the second branch of the carrier channel, towards the junction of the sample channel while the sample liquid is introduced into the carrier channel through the junction.

13. The method of claim 12, wherein the reaction vessel contains a chemical reaction.

14. The method of claim 12, wherein the reaction vessel contains a biological reaction.

* * * * *